US006921412B1

(12) United States Patent
Black et al.

(10) Patent No.: US 6,921,412 B1
(45) Date of Patent: Jul. 26, 2005

(54) SELF-SUPPORTING, SHAPED, THREE-DIMENSIONAL BIOPOLYMERIC MATERIALS AND METHODS

(75) Inventors: Kirby S. Black, Acworth, GA (US); K. Umit Yuksel, Kennesaw, GA (US); Aaron J. Trygstad, Smyma, GA (US)

(73) Assignee: Cryolife, Inc., Kennesaw, GA (US)

( * ) Notice: Subject to any disclaimer, the term of this patent is extended or adjusted under 35 U.S.C. 154(b) by 0 days.

(21) Appl. No.: 09/570,600

(22) Filed: May 12, 2000

Related U.S. Application Data

(60) Provisional application No. 60/134,624, filed on May 18, 1999.

(51) Int. Cl.[7] ............................................. A61B 17/08
(52) U.S. Cl. ..................................................... 606/213
(58) Field of Search ................................. 606/213, 214

(56) References Cited

U.S. PATENT DOCUMENTS

| | | |
|---|---|---|
| 4,247,406 A | 1/1981 | Widder et al. |
| 4,342,636 A | 8/1982 | Chang et al. |
| 4,822,361 A | 4/1989 | Okita et al. ................... 623/12 |
| 5,132,108 A | 7/1992 | Narayanan et al. |
| 5,171,574 A | 12/1992 | Kuberasampath et al. |
| 5,272,074 A | 12/1993 | Rubens |
| 5,324,647 A | 6/1994 | Rubens et al. |
| 5,326,568 A | 7/1994 | Giampapa |
| 5,344,451 A | 9/1994 | Dayton |
| 5,510,121 A | 4/1996 | Rhee et al. |
| 5,510,418 A | 4/1996 | Rhee et al. ................. 525/54.2 |
| 5,529,913 A | 6/1996 | Clayton et al. |
| 5,549,664 A | 8/1996 | Hirata et al. .................... 623/1 |
| 5,584,875 A | 12/1996 | Duhamel et al. ............... 623/1 |
| 5,585,116 A | 12/1996 | Boniface et al. |
| 5,591,224 A | 1/1997 | Schwartz et al. |
| 5,609,631 A | 3/1997 | Rubens et al. |
| 5,630,842 A | 5/1997 | Brodniewicz |
| 5,660,857 A | 8/1997 | Haynes et al. |
| 5,665,114 A | 9/1997 | Weadock et al. |
| 5,693,098 A | 12/1997 | Rubens et al. |
| 5,763,411 A | 6/1998 | Edwardson et al. |
| 5,766,584 A | 6/1998 | Edelman et al. ............ 424/93.7 |
| 5,770,417 A | 6/1998 | Vacanti et al. |
| 5,773,577 A | 6/1998 | Cappello |
| 5,836,313 A * | 11/1998 | Perez et al. .................. 128/898 |
| 5,932,659 A * | 8/1999 | Bambara et al. ............. 525/240 |
| 6,217,603 B1 * | 4/2001 | Clark et al. .................. 606/214 |
| 6,270,530 B1 * | 8/2001 | Eldridge et al. ............. 606/213 |
| 6,391,049 B1 * | 5/2002 | McNally et al. ............. 606/214 |

FOREIGN PATENT DOCUMENTS

| | | | |
|---|---|---|---|
| EP | 0 349 505 | 1/1990 | ........... A61L/27/00 |
| EP | 0 621 044 A2 | 10/1994 | ........... A61L/27/00 |
| WO | WO94/01508 | * 1/1994 | |
| WO | WO 99/09149 | 2/1999 | ........... C12N/11/00 |

OTHER PUBLICATIONS

XP–002217022; Section Ch, Week 198520; Anonymous: "Modification of flexible fabrics, leather and webs—by Impregnation with aq. Plastics dispersion and heat coagulation of dispersed plastic"; abstract; & Research Disclosure; vol. 252, No. 029, Apr. 10, 1985, Emsworth, GB.

* cited by examiner

*Primary Examiner*—Ismael Izaguirre
(74) *Attorney, Agent, or Firm*—Nixon & Vanderhye P.C.

(57) ABSTRACT

Self-supporting, shaped, three-dimensional cross-linked proteinaceous biopolymeric materials that may be implanted in vivo, and methods of making such materials are disclosed. The biopolymeric materials most preferably include reinforcing media, such as biocompatible fibrous or particulate materials. In use, the preformed, shaped biopolymeric materials may be applied to tissue in need of repair and then sealed around its edges with a liquid bioadhesive. In such a manner, repaired tissue which is capable of withstanding physiological pressures may be provided.

57 Claims, 2 Drawing Sheets

SELF-SUPPORTING, SHAPED, THREE-DIMENSIONAL BIOPOLYMERIC MATERIALS AND METHODS

CROSS-REFERENCE TO RELATED APPLICATION

This application is based on, and claims domestic priority benefits under 35 USC §119(e) from, U.S. Provisional Patent Application Ser. No. 60/134,624 filed on May 18, 1999, the entire content of which is incorporated expressly hereinto by reference.

FIELD OF THE INVENTION

The present invention is embodied generally in self-supporting, shaped, three-dimensional cross-linked proteinaceous biopolymeric materials that may be implanted in vivo, and in the methods of making such materials.

BACKGROUND AND SUMMARY OF THE INVENTION

Surgical adhesive compositions for tissue are well known as evidenced, for example, by U.S. Pat. No. 5,385,606 (the entire content of which is expressly incorporated hereinto by reference). In general, such surgical adhesives are achieved by combining a two part system typically comprised of a water soluble proteinaceous material (e.g., albumin, particularly bovine or human serum albumin), and a di- or polyaldehyde (e.g., glutaraldehyde) in appropriate amounts, and allowing the combined mixture to react in situ on the tissue surface or surfaces to be bonded. In this manner, sutureless (or minimally sutured) repairs of tissue wounds, perforations, tears and the like may be achieved.

Some tissue wounds, tears, and/or perforations are too large and/or complex to allow for the in situ reaction and repair by conventional biocompatible surgical adhesives. Thus, it would be highly desirable if pre-formed solid self-supporting, shaped, three-dimensional biocompatible materials possessing sufficient physical strength properties were provided which could be implanted in vivo and thereby enable physicians to repair tissue wounds, tears and/or perforations that are too large and/or complex to allow repair by conventional bioadhesives. It is towards fulfilling such needs that the present invention is directed.

Broadly, the present invention is embodied in self-supporting, shaped, three-dimensional cross-linked proteinaceous biopolymeric materials that may be implanted in vivo, and in the methods of making such materials. Most preferably, the biopolymeric materials of this invention are shaped to allow implantation in vivo. Specifically, according to one preferred embodiment of this invention, the biopolymeric materials of this invention may be cast onto suitable smooth casting surfaces, such as, for example, surfaces formed from stainless steel, aluminum, glass or polymeric (e.g., Lexan® polycarbonate) to make sheets of desired thickness.

According to one preferred embodiment of the invention, the shaped biopolymeric materials may integrally include reinforcing media, such as biocompatible fibrous or particulate materials. If used, the fibrous reinforcing media may be in the form of individual fibers, filaments, rovings and/or yarns embedded into the biopolymeric materials. Alternatively (or additionally), the fibrous reinforcing media may be in the form of woven or non-woven fabric or web structures which are embedded physically within the biopolymeric materials. The reinforcing media may also be in the form of particulate media that may be used alone or in combination with the fibrous reinforcing media.

The biomaterial structures of the present invention may be subjected to a variety of aftertreatments in order to achieve desired physical and/or chemical properties. For example, the tensile strength, flexibility, transparency, texture, biological (e.g., protease) resistance, chemical resistance and the like, may be engineered by virtue of such aftertreatments to suit particular end-use applications. In this regard, the aftertreatments may include, for example, bringing the biomaterial structure into contact with a desired treatment liquid, such as water or an organic liquid (e.g., alcohol, urea or glutaraldehyde solutions). Aqueous solutions of a salt (e.g., sodium chloride) have also been found to affect the biomaterial structure's resistance to proteolysis.

The biomaterial structures of the present invention may also be rendered porous, if desired. Specifically, a dissolvable particulate medium (e.g., calcium carbonate) may be dispersed throughout the biomaterial structure as briefly described above. The particulate-laden biomaterial structure may then be brought into contact with a suitable solvent for the particulate medium so as to dissolve a sufficient amount of the same to render the biomaterial structure porous. For example, when employing calcium carbonate as the particulate medium, the biomaterial structure may be brought into contact with hydrochloric acid sufficient to dissolve an amount of the calcium carbonate and render the structure porous. That is, pores will remain in the biomaterial structure following dissolution of the particulate medium.

These and other aspects and advantages of the present invention will become more clear after careful consideration is given to the following detailed description of the preferred exemplary embodiments thereof.

BRIEF DESCRIPTION OF THE ACCOMPANYING DRAWINGS

The accompanying drawing FIGURES depict preferred embodiments of the present invention wherein.

DETAILED DESCRIPTION OF THE INVENTION

Figure 1:
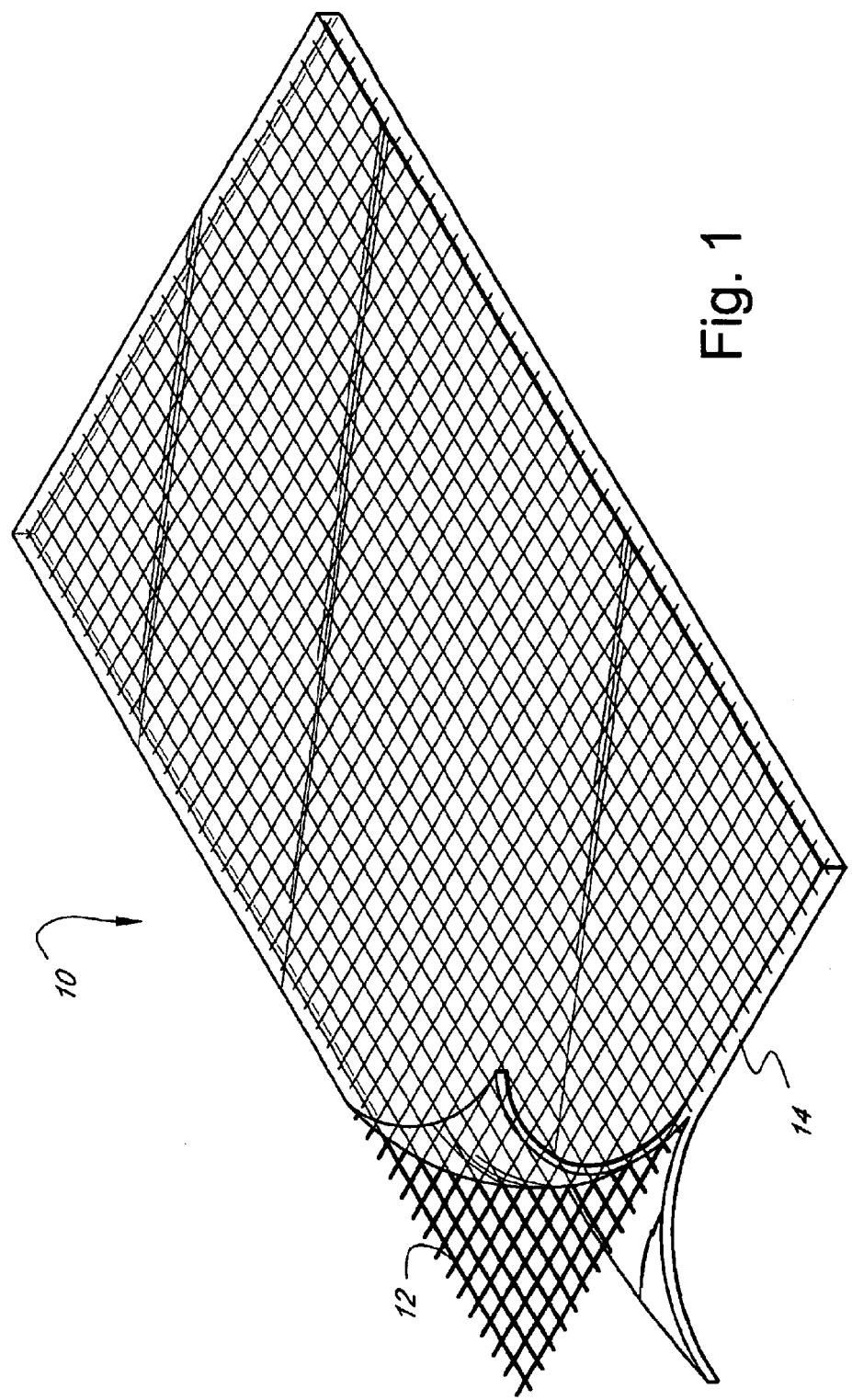
FIG. 1 is a schematic representation of an exemplary sheet form of the biomaterial structure in accordance with the present invention.

The term "self-supporting" as used herein and in the accompanying claims means that the material is sufficiently solid and has adequate inherent mechanical integrity to maintain its shape in the absence of external supporting structure.

A "three-dimensional" structure is one which is molded, cast, extruded or otherwise shaped into a desired geometric shape. Three-dimensional structures of this invention may be relatively simple such as flat sheets of desired thickness which can be subsequently formed into other geometries, such as tubes, cylinders, cones and the like. The biopolymeric materials of this invention can also be formed into complex shapes in dependence upon the particular mold cavity that is employed.

The self-supporting, shaped, three-dimensional biopolymeric materials of this invention are most preferably the cross-linked reaction product of a two part mixture initially comprised of:

Part A: a water-soluble proteinaceous material of about 27–53% by weight of the mixture, and Part B: di- or polyaldehydes present in a weight ratio of one part by weight to every 20–60 parts of protein present by weight in the mixture and water, optionally containing non-essential ingredients to make up the balance of the composition.

Part A of the mixture is most preferably substantially an aqueous solution of a proteinaceous material of human or animal origin. Albumins including ovalbumins are preferred proteins, and serum albumins of human or animal origin are particularly preferred. The proteinaceous material may be a purified protein or a mixture in which the proteins such as serum albumins are the predominant ingredients. For example, the solid mixtures obtained by dehydration of blood plasma or serum, or of commercial solutions of stabilized plasma proteins, can be used to prepare Part A. These mixtures, generally referred to as plasma solids or serum solids, are known to contain albumins as their major ingredients, of the order of 50–90%. As used herein, the term "plasma" refers to whole blood from which the corpuscles have been removed by centrifugation. The term "serum" refers to plasma which has additionally been treated to prevent agglutination by removal of its fibrinogen and/or fibrin, or by inhibiting the fibrin clot formation through addition of reagents, such as citrate or EDTA. The proteinaceous material may also contain an effective amount of hemoglobin.

Part B of the adhesive composition is substantially an aqueous solution of di- or polyaldehydes. A wide range of these substances exist, and their usefulness is restricted largely by availability and by their solubility in water. For example, aqueous glyoxal (ethandial) is useful, as is aqueous glutaraldehyde (pentandial). Water soluble mixtures of di- and polyaldehydes prepared by oxidative cleavage of appropriate carbohydrates with periodate, ozone or the like are also useful. Glutaraldehyde is the preferred dialdehyde ingredient of Part B. When Parts A and B are brought together, the resultant product rapidly hardens to a strong, flexible, leathery or rubbery material within a short time of mixing, generally on the order of 15–30 seconds. The most preferred material for use in the present invention is commercially available from CryoLife, Inc. of Kennesaw, Ga. under the registered trademark "BIOGLUE".

The material will exhibit a tear strength of at least about 400 g/cm$^2$ when tested according to ASTM D638M-93 or ASTM D882-95a. Significant improvements to tear strengths, and other physical properties of the material, are realized by imbedding a fibrous reinforcing material physically within the biopolymeric material. In this regard, the mixture of Parts A and B is most preferably brought into contact with the reinforcing material so that, upon solidification of the mixture, the reinforcing material is physically embedded therewithin. Thus, the reinforcing material may be pre-disposed in a desired shaped configuration on a mold or casting surface so that subsequent introduction of the liquid Part A and Part B mixture will saturate the same and cause the reinforcing material to become a part of, and assume the shape of, the resulting solid, self-supporting biopolymeric material.

The particular fibrous reinforcing material that is employed is not critical, provided it is biologically compatible. Thus, natural or synthetic fibers, such as polyesters, nylons, polyolefins, glass and the like of virtually any desired denier may be employed. Furthermore, the reinforcing fibers may be used in the form of a continuous length of single fibers (i.e., monofilaments) or a yarn, roving or rope of multiple filaments. Moreover, the reinforcing media may be in the form of staple fibers of predetermined lengths which are spun into yarns, rovings and/or ropes of desired denier and continuous length. The mono- or multifilamentary reinforcing materials may also be in the form of woven or non-woven fabric structures. Suffice it to say here, that virtually any physical form of fibrous reinforcing material may be satisfactorily employed in the practice of the present invention.

The reinforcing material may also be in the form of particulates, such as synthetic or natural organic and inorganic particulate reinforcement materials. Some representative examples of such particulates include calcium carbonate, calcium phosphate, hydroxyapatite bone chips, ceramic particles and the like. Most preferably, the particulate reinforcement material will have a nominal particulate size of between about 1 µm to about 7 mm, and will be present in the biomaterial in an amount effective to provide the desired reinforcement or other properties while not adversely affecting the biomaterial's self-supporting three-dimensional characteristics.

The accompanying drawing FIG. 1 depicts a particularly preferred sheet 10 of self-supporting, three-dimensional biomaterial in accordance with the present invention. As shown, the sheet 10 includes a reinforcing medium 12 comprised of a woven fibrous scrim fabric which is embedded within and encased by a layer of cured cross-linked proteinaceous material 14 having a desired thickness. In this regard, the accompanying FIGURE depicts, for illustration purposes only, portions of the proteinaceous material forming the sheet 10 having been "peeled" away from the embedded reinforcing medium 12, it being understood in practice the reinforcing medium 12 is most preferably completely embedded within a unitary thickness of the cured biomaterial 14.

The biomaterial may be shaped in any convenient manner. Thus, when forming flat sheet materials, the components of Parts A and B may be cast as a batchwise mixture onto a planar surface and then doctor-bladed to the proper thickness. That is, parallel laterally separated guides may be provided on the casting surface so as to support the terminal ends of a doctor blade. By moving the doctor blade along the guides, a sheet of the biomaterial having the same thickness as that of the guides will result.

The biomaterial may also be continuously cast into sheets using conventional continuous casting techniques. Thus, for example, the liquid mixture of Parts A and B may be extruded through a slit nozzle onto a rotating drum casting surface. The resulting cast sheet may be processed between nip rollers for thickness control and wound onto a take-up drum for further processing.

Reinforcing fabric media, if desired, may be positioned on the casting surface prior to batch casting of the liquid biomaterial mixture thereby causing the former to be encapsulated within the latter upon curing. When using continuous casting techniques, the reinforcing fabric material may be unwound from a supply spool onto the surface of the casting roll so that the biomaterial may be extruded thereonto. If using particulate reinforcing media, a suitable supply means may be provided so that the particulates are introduced into the uncured biomaterial.

The sheet material that is formed may be wet with a suitable liquid (e.g., water, alcohol or the like) so as to decrease its surface tension and thereby permit it to be more easily removed from the casting surface.

Sheet thicknesses of the biomaterial according to this invention, whether reinforced or not, are most preferably between about 0.1 mm to about 1.5 mm.

Figure 2B:
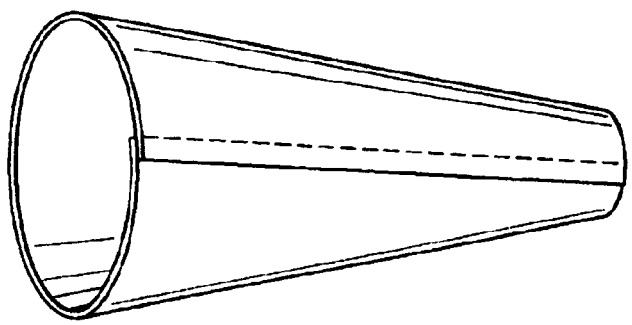
FIGS. 2A and 2B show exemplary preferred cylindrical and conical geometric forms of the biomaterial structure in accordance with the present invention, respectively.
Figure 2A:
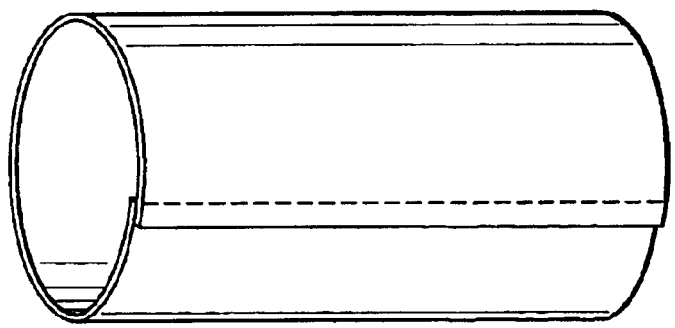

The sheets as depicted in FIG. 1 may be fashioned into other geometrical configurations as shown in FIGS. 2A and 2B. Thus, for example, the sheets may be rolled or otherwise configured into generally cylindrical (FIG. 2A), conical (FIG. 2B) and like geometric configurations by overlapping opposed edge regions of the sheet. The overlapped edge regions may be joined to one another using additional quantities of liquid mixture comprised of Parts A and B. Compound shapes may also be made. Thus, for example, a proximal conical segment may be joined to a distal cylindrical segment. Suffice it to say here that virtually any three-dimensional shaped structure may be fabricated from the biomaterial of this invention.

The biomaterial may also be shaped by suitable molding techniques. Thus, for example, a suitably configured mold cavity may be provided into which the liquid mixture of Parts A and B may be injected. Upon curing, the resulting external surface of the biomaterial will assume the configuration of the mold cavity. Suitable inserts may likewise be provided so that internal surfaces can be molded into the shaped part.

The preformed, self-supporting, three-dimensional biomaterial structures of this invention may be used for the sutureless (or minimally sutured) repair of tissue wounds, perforations, tears and the like. Thus anastomotic techniques to repair severed tissue, such as vascular vessels, may be accomplished using the biomaterial components of this invention in the form of sheets, cylinders, cones, tube or other suitable geometric structures. In practice, therefore, a suitable self-supporting, three-dimensional biomaterial component may be brought into covering relationship with the tissue laceration, wound, sever, perforation, tear or the like and then fixed to the surrounding tissue via a suitable bioadhesive material. A minimal number of sutures may also be employed so as to initially positionally fix the biomaterial component relative to the tissue site undergoing repair. The preformed biomaterial component of this invention may then be sealed around its edges to the tissue to as to provide a fluid-tight seal which is capable of withstanding physiological pressures.

Further understanding of this invention will be gained from the following non-limiting Examples.

EXAMPLES

Example 1

A rectangular glass plate having a flat, non-stick casting surface was used for casting sheets of biomaterial. The top of the glass plate was open and included a sliding bar as a doctor blade supported on a pair of laterally spaced-apart parallel guides having a thickness of about 0.4 mm. A large aliquot of liquid BioGlue® proteinaceous material (CryoLife, Inc., Kennesaw, Ga.) was deposited onto the casting surface near the doctor blade. The doctor blade was moved along the guides so as to spread the liquid mixture evenly along the casting surface. Upon curing, the resulting sheet of biomaterial had a substantially uniform thickness of about 0.4 mm.

Example 2

A generally circular pool (approx. 3 inches in diameter) of liquid BioGlue® proteinaceous material was dispensed onto a surface of a plastic sheet. A piece of fiberglass fabric was then placed on the pool while the material was still liquid, followed by a second layer of plastic sheet. This sandwich structure was then compressed by the weight of a book. After curing, the resulting reinforced biomaterial sheet was easily peeled form the plastic forming sheets and was placed in water to prevent dehydration. The reinforced biomaterial film was observed to be extremely strong, while maintaining a great deal of flexibility and memory.

Example 3

Example 2 was repeated using Vicryl™ (Ethicon) knitted polyester mesh. Similar results were achieved as with Example 1. The material of this Example 2, however, was somewhat more flexible, probably owing to the relatively soft nature of the woven mesh that was employed as the reinforcing medium. This material was pressure tested and was shown to withstand>700 mm Hg.

Example 4

Cones were constructed from the sheet materials formed according to Example 3 by cutting several small (approx. ¼-inch diameter circle) or generally isosceles-shaped triangular pieces from approximately 1 mm thick sections of the reinforced biomaterial film and folding the pieces into a generally conically shaped components. The overlapped edges of these components were tack-sutured (between 3 to 4 sutures) using 6-0 Prolene™ suture thread. An additional aliquot of BioGlue® proteinaceous material was applied over the tack-sutured edges to seal them to one another. The resulting segmented conically shaped components had an apex opening of about 2–3 mm and an distal opening of about 3 cm. These components were observed to be extremely flexible and did not break or fracture when subjected to bending and folding. Also, the conically shaped components could be compressed and exhibited sufficient shape-retention memory such that they returned to their native shape once the compressive force was released.

Example 5

Example 4 was repeated except that generally cylindrical components were made. Similar physical properties were observed.

Example 6

Example 4 was repeated, except that no reinforcing medium was employed. The cones were positioned over respective severed vascular vessel segments to be anastomosed. The vessels to be joined had a catheter inserted distally and oriented to positionally retain the terminal ends of the severed vessels in opposition to one another and allow communication between the vessels when removed. The large open ends of the opposed cones positioned on each vascular vessel were overlapped so as to enclose the terminal ends of the severed vessels within the resulting hollow interior space of the joined cones. A needle was inserted through one of the cones into the interior space to allow liquid BioGlue® proteinaceous material to be injected thereinto until the space was filled. The material was allowed to cure for several minutes, following which the catheter was removed. The vessel was thereafter pressurized to test the fluid communication and strength of the anastomosis and withstood a pressure estimated to be between about 300 to about 400 mm Hg.

Example 7

Figure 3:
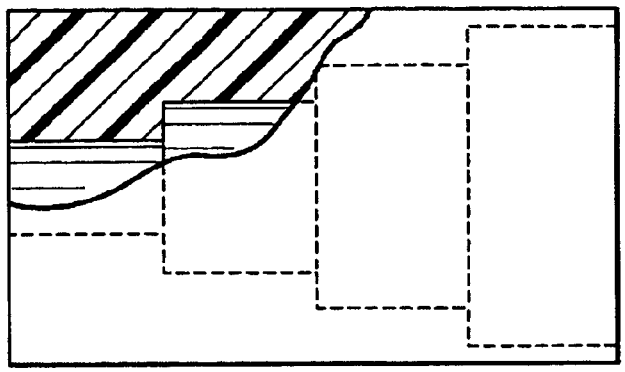
FIG. 3 shows a geometric form, partly in section, of the biomaterial structure in accordance with Example 7 below.

A conventional laboratory hose barb was positioned within a syringe barrel. The space between the exterior surfaces of the hose barb and the interior surface of the syringe barrel wall was then filled with liquid BioGlue® proteinaceous material. After curing, the resulting molded biomaterial component had a cylindrical outer surface with a hollow interior formed of coaxially aligned, stepped cylindrical segments from about ½ diameter at one end to about ⅛ inch diameter at the opposite end (see FIG. 3). This component could be used for anastomosis applications whereby it could be cut latitudinally to expose the proper interior hollow diameter sized to match the vessel undergoing anastomosis.

Example 8

A ring-shaped film structure formed of cured BioGlue® proteinaceous material was used to anchor a vessel that would be used in a coronary bypass procedure. In this regard, it is theorized that the vessel could be secured to the surface of a beating heart via the ring-shaped film structure where coronary bypass could be completed.

Example 9

Example 8 was repeated except with larger tubing in order to produce a self-supporting tube having an inner diameter of 14 mm and an outer diameter of 16 mm. Following this preparation, a fiberglass-reinforced piece of the biopolymeric material was additionally secured to the exterior of the self-supporting tube with BioGlue® proteinaceous material. This reinforced tube was then anastomosed to a porcine aorta obtained from a slaughterhouse. The anastomosis was done using 3-0 Prolene™ to tack suture the ends together, and was reinforced with BioGlue® proteinaceous material. This junction was then pressure tested and was found to hold a pressure greater than 250 mm Hg.

Example 10

An axially tensioned inner PTFE (polytetrafluoroethylene) tube having a 1 mm outside diameter was positioned concentrically within an outer tube having an inside diameter of 2.5 mm using an axially separated pair of polypropylene spacers. An annular space of about 1.5 mm and extending about 15 cm axially was thereby defined between the concentrically positioned pair of tubes. Both the inner and outer tubes were lubricated with petroleum jelly to enhance the release of the tube from the molded biomaterial. Liquid BioGlue® proteinaceous material was then introduced into the annular space and allowed to cure. After fully curing, a self-supporting tube having a length of about 15 cm, with an outside diameter of about 2.5 mm and an inside diameter of about 1.0 mm was obtained.

Example 11

Relatively thin non-reinforced sheets of biomaterial were prepared by introducing liquid BioGlue® proteinaceous material between a pair of glass plates separated by suitable spacers of either 0.75 mm, 0.40 mm and 0.25 mm thick. In general, cooling the plates to about 4° C. and/or using glutaraldehyde in the amount of 5 wt.% enabled thinner sheets to be made.

Example 12

Sheets of biomaterial were made by depositing a pool of liquid BioGlue® proteinaceous material onto a suitable casting surface in an amount sufficient to obtain the desired sheet thickness. Particularly, biomaterial sheets having nominal thicknesses of 0.2 mm and 0.75 mm thick were made. To test the usefulness of these sheets, porcine lung and liver tissue was obtained from a slaughterhouse. The tissue was warmed by immersion in hot water for several seconds to simulate in vivo physiological conditions. Once the tissue was warmed and dried, the biomaterial sheets were adhesively bonded over lacerations on the surface of the tissue using additional liquid BioGlue® proteinaceous material as a bioadhesive. The repair was tested by slightly pressurizing each tissue with a tire pump beyond physiological air pressure of 15–20 mm $H_2O$ water column. Neither tissue is normally under extreme pressure, but the leak test that was performed proved that the biomaterial sheet patches held, regardless of whether the bioadhesive was applied around or under the sheet patch.

Example 13

Example 12 was repeated except that several tacking sutures were applied through the biomaterial sheet patches reinforced with fiberglass and Vicryl® polyester meshes to provide a preliminary positional fixation onto the tissue surface. Subsequent application of liquid BioGlue® proteinaceous material around and on top of the patch edges served to provide a sealed repair to the lacerated tissue.

Example 14

Reinforced biopolymeric material was produced by suspending hydroxyapatite in BioGlue® proteinaceous material. The particulate-rich BioGlue® proteinaceous material was cast into rods and was tested for mechanical properties. A linear increase with particulate concentration was seen in the elastic modulus of reinforced materials to>200% of particulate-free biopolymeric material. The concentration of hydroxyapatite tested ranged from 2 to 35 wt % of the protein solution composition.

Example 15

Example 14 was repeated, but the hydroxyapatite was replaced with calcium carbonate. Again, the reinforced material was tested for mechanical properties. A linear increase with particulate concentration was seen in the elastic modulus of reinforced materials to >200% of particulate-free biopolymeric material. The concentration of calcium carbonate tested ranged from 2 to 65 wt % of the protein solution composition.

Example 16

Example 15 was repeated, but the reinforced biopolymeric material was treated with a solution of 6 molar hydrochloric acid to dissolve the calcium carbonate. After incubation, the biopolymeric material was seen to be porous as a result of the calcium carbonate's dissolution.

Example 17

Sheets of biomaterial were made by depositing a pool of liquid BioGlue® proteinaceous material onto a suitable casting surface in an amount sufficient to obtain desired sheet thickness. Particularly, sheets of 0.4 mm thickness were made. The biomaterial sheet was further processed by cutting into several pieces to obtain identical units. These units were either kept sealed in polyethylene pouch or soaked in water or in glutaraldehyde solutions (0.01 to 1 vol %). These treated samples were then digested with trypsin to assess their relative resistances to proteolysis. The water-soaked samples could be digested by the trypsin, while the glutaraldehyde-soaked samples were quite resistant to proteolysis.

Example 18

Example 17 was repeated, but the units were treated in solutions of varying sodium chloride concentration (0.5 to 5.0 molar). These treated samples were then digested with trypsin to assess their relative resistances to proteolysis. The extent of digestion was shown to be inversely related to the sodium chloride concentration.

Example 19

Sheets of biomaterial were made by depositing a pool of liquid BioGlue® proteinaceous material onto a suitable casting surface in an amount sufficient to obtain desired sheet thickness. One of these sheets (0.67 mm in thickness) was positioned between two cells of a diffusion chamber as a membrane. These two cells were then filled with water. Methylene blue was added to one chamber, and the other side was monitored spectroscopically for the diffusion of methylene blue across the membrane. The colorless chamber showed evidence of methylene blue diffusion at 5 hours.

Example 20

Casts of biomaterial were produced by injecting liquid BioGlue® proteinaceous material into a suitable cylindrical mold in an amount sufficient to fill the mold. The casts were immersed in water, and the dimensions monitored. The material increased in weight and in volume by about 10%.

Example 21

Example 20 was repeated, but the casts were immersed in mono- and poly-functional alcohols (e.g., 100% glycerol or n-propanol). The material was seen to lose weight by 50% in each case, with a similar decrease in volume. This loss was mainly due to dehydration and not decomposition.

Example 22

Example 21 was repeated, but the casts were immersed in 5 wt % urea. The material's weight increased by 10% and the volume by greater than 25%. In addition, the casts had been further changed to a very soft material.

Example 23

Sheets of biomaterial were made by depositing a pool of liquid BioGlue® proteinaceous material onto a suitable casting surface in an amount sufficient to obtain desired sheet thickness. Glutaraldehyde concentration of these sheets varied between 5 and 10 wt % of the cross-link solution composition. These sheets were then sealed in polyethylene pouches filled with water. Half of these sheets were sent out for gamma-irradiation. The two sets of sheets were then tested for mechanical properties. The irradiated and unirradiated sheets had similar tensile strengths and elastic moduli. The sheets with glutaraldehyde concentrations at 5 wt. % and 10 wt. % had tensile strengths of 1200 and 3500 gf/cm$^2$ and elastic moduli of 5 and 30 kgf/cm$^2$, respectively.

Example 24

Biomaterial was produced with chondroitin sulfate that was dissolved in BioGlue® proteinaceous material. The chondroitin sulfate was detectable via a complexation reaction with alcian blue, and showed that this glycosaminoglycan could be eluted from the biomaterial.

Example 25

Example 1 was repeated using bovine hemoglobin instead of albumin. The resulting material was soft and pliable. The material was made into thin sheets per Example 1, and was shown to have a tensile strength of 3000 g f/cm$^2$ and an elastic modulus of 30 kgf/cm$^2$.

Example 26

Reinforced biomaterial was produced by attaching a tubular piece of coarse nylon or polyester mesh to a plastic rod. The plastic rod was then rolled in liquid BioGlue® proteinaceous material to evenly coat the mesh. While the mesh had no water holding ability, the new biomaterial was water tight. Testing the burst strength of these vessels showed that they could withstand pressures of 300 to 400 mm of Hg.

Example 27

A bone-shaped mass of biomaterial was made using a commercially-available plastic model. BioGlue® proteinaceous material was cast into a negative mold of the bone-shape model and then cured. The biomaterial was successfully removed from the mold, and closely resembled the appearance of the model.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A biomaterial structure which includes a biopolymeric member consisting of a pre-formed, self-supporting, shaped, three-dimensional cross-linked proteinaceous biopolymeric material.

2. The biomaterial structure of claim 1, which further includes a fibrous and/or particulate reinforcing medium adhered to said biopolymeric member.

3. The biomaterial structure of claim 2, wherein said fibrous reinforcing medium includes natural or synthetic fibers.

4. The biomaterial structure of claim 2, wherein said fibrous reinforcing medium includes a fabric formed of natural or synthetic fibers.

5. The biomaterial structure of claim 4, wherein the fabric is a woven fabric.

6. The biomaterial structure of claim 4, wherein the fabric is nonwoven.

7. A biomaterial structure which includes:
   (i) a biopolymeric member consisting of a pre-formed, self-supporting, shaped, three-dimensional cross-linked proteinaceous biopolymeric material;
   (ii) a particulate reinforcing medium adhered to said biopolymeric member, said particulate reinforcing medium having a nominal particle size of between about 1 µm to about 7 mm, and optionally
   (iii) a fibrous reinforcing medium.

8. The biomaterial structure of claim 1 or 7, wherein said biopolymeric member is porous.

9. A biomaterial structure which includes:
   (i) a biopolymeric member consisting of a pre-formed, self-supporting, shaped, three-dimensional cross-linked proteinaceous biopolymer which is the cross-linked reaction product of human or animal-derived protein material and a di- or polyaldehyde, and
   (ii) a fibrous and/or particulate reinforcing medium embedded in said biopolymeric member.

10. The biomaterial structure of claim 9, wherein said fibrous reinforcing medium includes natural or synthetic fibers.

11. The biomaterial structure of claim 10, wherein said fibrous reinforcing medium includes a fabric formed of natural or synthetic fibers.

12. The biomaterial structure of claim 11, wherein the fabric is a woven fabric.

13. The biomaterial structure of claim 11, wherein the fabric is nonwoven.

14. A biomaterial structure which includes:
(i) a biopolymeric member consisting of a pre-formed, self-supporting, shaped, three-dimensional cross-linked proteinaceous biopolymer, and
(ii) a particulate reinforcing medium embedded within said biopolymeric member, wherein the particulate reinforcing medium has a nominal particle size of between about 1 $\mu$m to about 7 mm.

15. The biomaterial structure of claim 14, wherein said biopolymer is the cross-linked reaction product of human or animal-derived protein material and a di- or polyaldehyde.

16. The biomaterial structure of claim 9 or 15, wherein the protein is bovine or human serum albumin or hemoglobin.

17. The biomaterial structure of claim 16, wherein the aldehyde is glutaraldehyde.

18. A method of making a biomaterial structure comprising forming a biopolymeric member which consists of a self-supporting, shaped, three-dimensional cross-linked proteinaceous biopolymeric material, and embedding within said biopolymeric material a fibrous and/or particulate reinforcing medium.

19. The method of claim 18, which includes placing the fibrous and/or particulate reinforcing material onto a casting surface, and then casting the biopolymeric material as a liquid onto the casting surface to form the bioplymeric member as a sheet of reinforced biomaterial.

20. The method of claim 19, which includes moving a doctor blade over the mass of liquid biopolymeric material to achieve a predetermined sheet thickness.

21. The method of claim 19, which includes forming the sheet of reinforced biomaterial into a generally conically or cylindrically shaped structure.

22. The method of claim 21, wherein said step of forming the sheet of reinforced biomaterial into a generally conically or cylindrically shaped structure includes overlapping edge portions of the sheet, and fixing said overlapped edge portions to one another.

23. The method of claim 22, wherein said step of forming the sheet of reinforced biomaterial into a generally conically or cylindrically shaped structure includes applying a liquid bioadhesive to said overlapped edges.

24. The method of claim 18, wherein said reinforcing medium is particulate, and wherein the method further comprises dissolving the particulate reinforcing medium to obtain a porous biopolymeric member.

25. The method of claim 18, which further comprises subjecting the biopolymeric member to an aftertreatment sufficient to obtain desired physical and/or chemical properties.

26. The method of claim 25, wherein the aftertreatment includes bringing the biopolmeric member into contact with a treatment liquid.

27. The method of claim 26, wherein the treatment liquid includes water or an organic liquid.

28. The method of claim 27, wherein the organic liquid includes alcohol, urea or glutaraldehyde solutions.

29. The method of claim 26, wherein the treatment liquid includes an aqueous solution of sodium chloride.

30. The method of claim 29, wherein the sodium chloride solution is between about 0.5 molar to 5.0 molar.

31. A method of making a porous biomaterial structure comprising the steps of (i) forming a biopolymeric member which consists of a self-supporting, shaped, three-dimensional cross-linked proteinaceous biopolymeric material, (ii) incorporating a dissolvable particulate medium within the biopolymeric material, and thereafter (iii) dissolving the particulate medium from the biopolymeric material to thereby render the biomaterial structure porous.

32. The method of claim 31, wherein said step of dissolving the particulate medium from the biopolymeric material includes bringing the biomaterial structure into contact with a liquid solvent for said particulate medium for a time sufficient to dissolve an amount of said particulate material to render the biomaterial structure porous.

33. The method of claim 32, wherein the particulate material includes calcium carbonate.

34. The method of claim 33, wherein the calcium carbonate is present in an amount between about 2 wt. % to about 65 wt. %.

35. The method of any one of claims 31–34, which comprises bringing the biomaterial structure in which the particulate material is dispersed into contact with an acid.

36. The method of claim 35, wherein the acid is hydrochloric acid.

37. A porous biomaterial made according to the method of claim 31.

38. A method of repairing damaged human or animal tissue in vivo, which comprises positioning a biomaterial structure which includes a biopolymeric member consisting of a preformed, self-supporting, three-dimensionally shaped biopolymer onto a tissue site in need of repair, and thereafter sealing edges of the biomaterial structure to the tissue by application of a bioadhesive.

39. The method of claim 38, wherein the biomaterial structure is in the form of a sheet, ring, tube, cylinder and/or cone.

40. The method of claim 38, wherein the biomaterial structure includes a fibrous or particulate reinforcing medium.

41. The method of claim 40, wherein the biomaterial structure is in the form of a sheet.

42. The method of claim 40, wherein the biomaterial structure is in the form of a tube, cylinder or cone.

43. The method of claim 40, wherein the biomaterial structure is in the form of a tube having a substantially constant outside diameter, and a variably stepped inside diameter.

44. The method of claim 40, further comprising placing at least one tack suture into the biomaterial structure to initially positionally fix the biomaterial structure to the tissue in need of repair.

45. The method of claim 38, wherein the biomaterial structure is porous.

46. A biomaterial structure which includes a biopolymeric member consisting of a pre-formed, self-supporting, shaped, three-dimensional cross-linked proteinaceous biopolymeric material which is the cross-linked reaction product of human or animal-derived protein material and a di- or polyaldehyde.

47. The biomaterial structure of claim 46, wherein the protein is bovine or human serum albumin or hemoglobin.

48. The biomaterial structure of claim 46, wherein the aldehyde is glutaraldehyde.

49. The biomaterial structure of claim 46, which includes a fibrous and/or particulate reinforcing medium adhered to said biopolymeric member.

50. The biomaterial structure of claim 49, wherein said fibrous reinforcing medium includes natural or synthetic fibers.

51. The biomaterial structure of claim 49, wherein said fibrous reinforcing medium includes a fabric formed of natural or synthetic fibers.

52. The biomaterial structure of claim 51, wherein the fabric is a woven fabric.

53. The biomaterial structure of claim 51, wherein the fabric is nonwoven.

54. The biomaterial structure of claim 49, wherein the particulate reinforcing medium has a nominal particle size of between about 1 μm to about 7 mm.

55. The biomaterial structure of claim 46, wherein said biopolymeric member is porous.

56. A method of making a reinforced biomaterial which comprises (i) embedding a fibrous and/or particulate reinforcing medium within a mass of liquid cross-linkable biopolymeric material, thereafter (ii) allowing the biopolymeric material to cross-link and thereby cure to form a sheet of self-supporting, fibrous and/or particulate reinforced biomaterial, (iii) forming the sheet of reinforced biomaterial into a generally conically or cylindrically shaped structure by overlapping edge portions of the sheet and fixing said overlapped edge portions to one another.

57. The method of claim 56, wherein step (iii) includes applying a liquid bioadhesive to said overlapped edges.

* * * * *